(12) United States Patent
Voipio et al.

(10) Patent No.: US 6,208,423 B1
(45) Date of Patent: Mar. 27, 2001

(54) ARRANGEMENT AT MEASUREMENT OF PH OR ANOTHER CHEMICAL PROPERTY DETECTABLE BY DYE INDICATORS

(75) Inventors: Ville Voipio; Katri Vuokila, both of Vantaa (FI)

(73) Assignee: Janesko Oy, Vantaa (FI)

( * ) Notice: Subject to any disclaimer, the term of this patent is extended or adjusted under 35 U.S.C. 154(b) by 0 days.

(21) Appl. No.: 09/328,263

(22) Filed: Jun. 17, 1999

(30) Foreign Application Priority Data

Jun. 18, 1998 (FI) .......................................... 981424

(51) Int. Cl.⁷ .................................................. G01N 21/47
(52) U.S. Cl. ................................................................ 356/446
(58) Field of Search .................................... 356/445, 446, 356/234, 432, 436, 409, 300, 326, 346, 345; 422/55, 57, 58, 82.05, 82.08, 82.09; 436/169

(56) References Cited

U.S. PATENT DOCUMENTS

| | | | |
|---|---|---|---|
| 3,992,158 | * 11/1976 | Przybylowicz et al. | 23/253 TP |
| 4,649,123 | 3/1987 | Charlton et al. | 436/79 |
| 5,039,491 | 8/1991 | Saaski et al. | 422/82.05 |
| 5,268,145 | 12/1993 | Namba et al. | 422/57 |
| 5,608,519 | * 3/1997 | Gourley et al. | 356/318 |

* cited by examiner

Primary Examiner—Frank G. Font
Assistant Examiner—Michael P. Stafira
(74) Attorney, Agent, or Firm—Burns, Doane, Swecker & Mathis, L.L.P.

(57) ABSTRACT

The invention relates to an arrangement at measurement of pH or another chemical property detectable by dye indicators. To provide a simple and safe solution, the measuring part is formed of a glass sheet or a similar substrate, the substrate being coated with a dye film, which is arranged to change its color in a manner known per se when a chemical property of the environment changes. The dye film is arranged to serve as a light reflective surface, whereby the chemical property of the solution to be measured can be measured as light reflection measurement.

7 Claims, 1 Drawing Sheet

Figure 1:
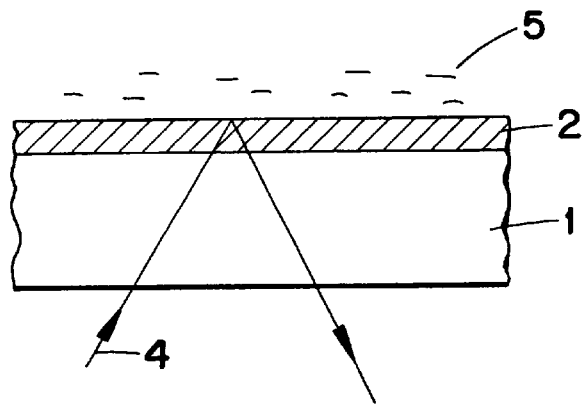

ARRANGEMENT AT MEASUREMENT OF PH OR ANOTHER CHEMICAL PROPERTY DETECTABLE BY DYE INDICATORS

FIELD OF THE INVENTION

The invention relates to an arrangement at measurement of pH or another chemical property detectable by dye indicators, the arrangement comprising a glass sheet or a similar substrate to be immersed into a solution to be measured, the substrate being coated with a dye film arranged to change its colour when a chemical property of the environment changes, and means for leading light through the substrate to the dye film.

BACKGROUND OF THE INVENTION

At measurement of pH in solutions, strips made of litmus paper, for instance, are generally used, the strips being immersed into a solution to be measured, whereby the paper changes its colour in accordance with the environment, i.e. the pH value of the solution.

In principle, the above procedure functions at least in some situations, for instance in laboratory conditions. However, a problem is the difficulty and slowness of the measurement. In addition, the procedure is inconvenient for example in certain industrial conditions. Another drawback of the above technique is its one-time nature. At present, glass membrane sensors based on electrochemical phenomena are mainly used for pH measurement in the industry.

SUMMARY OF THE INVENTION

The object of the invention is to provide an arrangement, by means of which the drawbacks of the prior art technique can be eliminated. This has been achieved by means of the invention. The arrangement of the invention is characterized in that the dye film is covered with a structure, comprising at least one layer, allowing ions to pass through and reflecting light backwards, whereby a colour change in the dye film can be measured as light reflection measurement.

The main advantage of the invention is its simplicity, which makes the introduction and use of the invention advantageous. Another advantage of the invention is that the measurement can be automated in an advantageous manner and, additionally, the measurement can preferably be performed directly in a process pipe as well.

BRIEF DESCRIPTION OF THE DRAWING FIGURES

Figure 2:
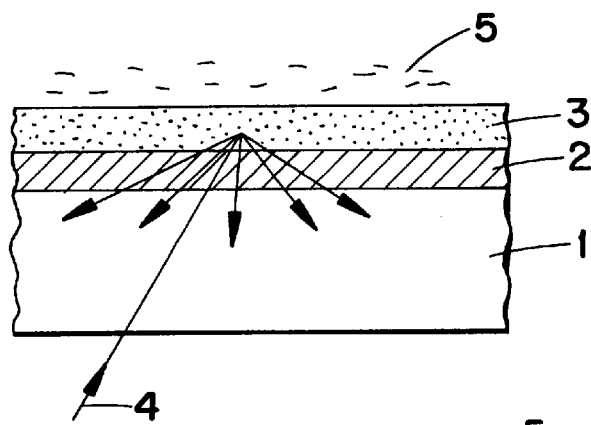
Figure 3:
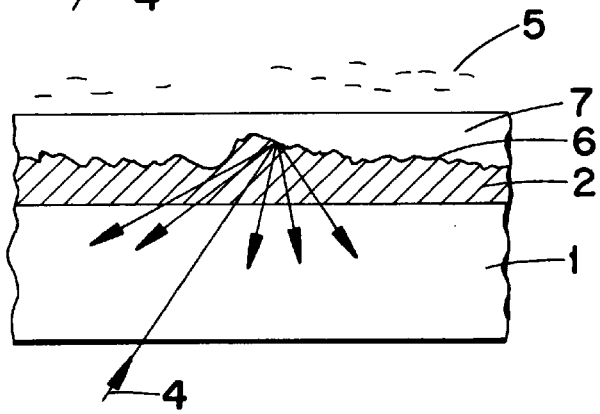
Figure 4:
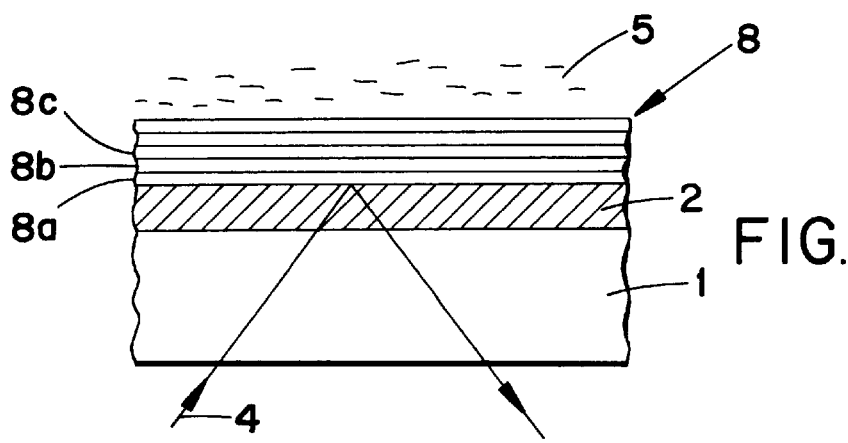

In the following, the invention will be described by means of preferred embodiments shown in the attached drawing, whereby FIG. 1 shows the basic principle of a first embodiment of an arrangement of the invention, FIG. 2 shows the basic principle of a second embodiment of the arrangement of the invention, FIG. 3 shows the basic principle of a third embodiment of the arrangement of the invention, and FIG. 4 shows the basic principle of a fourth embodiment of the arrangement of the invention.

DETAILED DESCRIPTION OF THE PREFERRED EMBODIMENT

As shown in the figures, the essential thing with the invention is that a glass sheet or a similar substrate 1 is coated with a dye film 2, which changes its colour in a manner known per se, when a chemical property, e.g. the pH value, of the environment changes. The dye of the dye film 2 may have for instance two states, viz. acid state and alkali state, having different colours and strengths. However, it shall be noted that the pH measurement is not the only application field of the invention, but the invention may also be applied for example to the measurement of the concentration of different metal ions in a solution.

FIG. 1 shows the essential basic principle of the invention. Light 4 is led through the substrate 1 to the dye film 2. The light can be a light beam or diffuse light. Reflection occurs from the interface between the dye film 2 and a solution 5 to be measured, such as process fluid. The reflection may be a partial or total reflection. Accordingly, the chemical property of the solution to be measured is measured by light reflection measurement, whereby only one optic window towards the process is needed. Consequently, the invention can be implemented in a rather simple manner.

The film mentioned above can preferably be fabricated of a solution synthesized by Sol-Gel method, described in more detail for instance in the book Sol-Gel Science, The Physics and Chemistry of Sol-Gel Processing, Academic Press, Inc. 1990. A Sol-Gel solution, i.e. a sol, is a solution which forms an inorganic polymer, glass, when drying on a glass surface. The glass sheet is coated for instance by immersing the sheet into the sol. The thickness and refractive index of the film are the most significant factors for the measuring optics. The thickness of the film is controlled by the viscosity of the sol and by immersion speed. The viscosity is changed by increasing or decreasing the amount of the solvent used and by changing the conditions of synthesis by means of a catalyst and the quantity of water, for example. Depending on the sol structure, the immersion speed has such an influence that, by slower immersion, a thinner film is produced, when the sol has a polymeric structure. If the sol has a particle structure, the film becomes thinner when the immersion speed increases. The refractive index of the film can be affected by the selection of sol precursor, i.e. the starting substance to be modified to metal oxide by other reagents, and by drying and filming conditions. The precursor forms an oxide, the refractive index of the oxide depending on the compound structure and metal atom. The refractive index of titanium oxide, for instance, is about 2, while the refractive index of silicon dioxide is about 1.5. Raising the drying temperature and making the film thinner raise the refractive index.

At Sol-Gel synthesis, as precursor serve in most cases metal alkoxides, which react easily with each other in the presence of a suitable catalyst or a gelatinating reagent and water. As catalyst can be used hydrochloric, nitric or sulphuric acid. Ammonia is also an often used catalyst. In turn, gelatinating reagents can be carboxylic acids, as an example of which acetic acid can be mentioned. The water can be added during the synthesis, it can be allowed to form through a reaction between a carboxylic acid and alcohol, or it can come from the humidity of air, the water reacting with the sol in the filming phase. By selection of catalyst, the polymerization and structure of the sol can be influenced. Alkali catalysts make a particulate sol, while acid catalysts make the sol polymeric. The quantity of water also affects the structure; if water is used in the molar ratio 2:1 with respect to an alkoxy mole and the catalyst is an acid, a polymeric sol is obtained.

Glass is the most generally used material in different optic components. Glass is often a stronger material than many plastics, which also are used relatively much in the optics at present. In comparison to plastics, the thermal resistivity of glass is in a class of its own. In the examples of the figures, glass has been used, but it shall be noted that the invention is not restricted to the use of glass only, but suitable plastics can naturally be used in the same way as is generally done in optics nowadays.

As described above, reflection measurement is utilized in the invention. FIG. 1 shows the basic principle applicable in different ways. FIGS. 2 and 3 show a second and a third embodiment of the invention. In the examples of the FIGS. 2 and 3, the essential thing is that the dye film 2 comprises a diffusely reflective surface disposed on it. In the case of FIG. 2, the diffusely reflective surface is a coating 3 compounded with pigments, whereby light is reflected from pigment particals. In the case of FIG. 3, the diffusely reflective surface is a rough surface 6. The structure also comprises a cover film 7 or several films on the rough surface. The rough surface 6 can be the rough surface of the dye film, as shown in FIG. 3, or the dye film surface can be smooth, but for instance the interface between the two following films rough, etc. Light 4 is reflected from the roughness of the interface diffusely. The layers as such are non-diffuse.

The pigment mentioned above can be either a substance added separately or pigment produced at the synthesis or in the manufacturing process. Instead of particles, small bubbles scattering light like particles are possible as well.

FIG. 4 shows an embodiment of the invention in which a dielectric mirror 8 is disposed on the dye film 2, which mirror may comprise one or several layers 8a, 8b, 8c. . . . The dielectric mirror can be manufactured for instance of two materials having very differing refractive indexes. The film structure, i.e. pack film, can preferably be made to a multilayer structure, whereby the pack film should have at least three layers. It is especially preferable to form a pack in such a way that it alternately comprises a layer having a high refractive index and a layer having a low refractive index. A single layer of titanium oxide alone reflects about 20% of the incident light, but the reflection gets essentially better when layers are added. A five-layer pack provides a reflection of about 70% already.

The thickness of the above layers may have an influence on in which wavelength range the film is reflective. The pack may be designed for one or several wavelengths. If two light beams are used for the measurement such that there is a big difference between the wavelengths of the light beams to be used, i.e. measuring beams, it is possible to form even two pack films on each other, designed separately for each wavelength.

In the example of FIG. 4, the dye film 2 is covered by a multilayer pack film, i.e. a dielectric mirror 8 composed of layers 8a, 8b and 8c. . . . The layers 8a, 8b, 8c . . . are arranged such that, next to the dye film 2, there is a material 8a having a high refractive index, then a material 8b having a low refractive index and then a material having a high refractive index etc. Reflection naturally occurs also on the glass interfaces between air and glass sheet and between glass sheet and dye film in the travel direction of the beam. Interface reflection between the glass sheet 1 and the dye film 2 can be decreased by fabricating the dye film 2 in such a way that it has the same refractive index as the glass to be used. The interface reflection between air and glass sheet can be decreased by coating that side of the glass sheet 1 with a material having a lower refractive index than the glass.

The function of a reflective pack film is based on interference. Two electromagnetic waves can be subjected to a constructive or deconstructive interference, depending on the phase of the waves with respect to each other. At the manufacture of a reflective film structure, the aim is to choose the thicknesses and refractive indexes in such a way that the interference will be constructive, whereby the reflected waves are in the same phase and the reflection is strong. If it is desirable to decrease the reflection, the thicknesses and refractive indexes are chosen such that the interference will be destructive, whereby the waves are in the opposite phases.

Layers disposed on the actual dye film can improve, besides reflective properties, also the mechanical resistance of the solution, by protecting the film against scratches and splits. In addition, they may lengthen the chemical duration of the film by decreasing the diffusion of dye molecules into the fluid to be measured. These layers can also be compounded with dye. As far as the porosity of the layers is concerned, the layers shall allow for instance the ions to be measured to pass through the film into contact with the dye of the dye film 2 and thus to react with it.

The above embodiments are by no means intended to restrict the invention, but the invention can be modified fully freely within the scope of the claims. It is thus clear that the arrangement of the invention or its details do not necessarily need to be just like shown in the figures, but solutions of another kind are also possible. Even if the examples of the figures present a glass sheet or the like, it is clear that this term shall be understood to cover, besides glass, also corresponding plastics and different parts; the glass sheet or the like can be a prism, for instance. The measuring beam or beams can be produced by means of any suitable light source. Any suitable indicator dyes can naturally be used in the dye film. Within the basic idea of the invention, layers on the dye film can be formed in any suitable manner, essential is only that the layers disposed on the dye film allow the OH and H ions of the solution to be measured to pass through and that the film simultaneously serves as a reflective surface, as described above. A diffusely reflective surface can be formed by means of different pigments, for instance. These materials can also be powdery additives, they can be produced from a reaction in accordance with the above, etc.

What is claimed is:

1. An arrangement at measurement of pH or another chemical property detectable by dye indicators, comprising:
   a substrate to be immersed into a solution to be measured, the substrate being coated with a dye film arranged to change its color when a chemical property of the environment changes, wherein the dye film is covered by a dielectric mirror formed of several layers, allowing ions to pass through and reflecting light backwards, whereby a color change in the dye film can be measured as light reflection measurement.

2. The arrangement according to claim 1, wherein the structure reflecting light backwards comprises a diffusely reflective surface.

3. The arrangement according to claim 2, wherein the diffusely reflective surface is a coating compounded with pigments.

4. The arrangement according to claim 2, wherein the diffusely reflective surface is a rough surface.

5. The arrangement according to claim 1, wherein the layers are composed of two different materials having very differing refractive indexes.

6. The arrangement according to claim 5, wherein the layers are arranged in such a way that, next to the dye film, there is a first material having a high refractive index, then a second material having a low refractive index.

7. The arrangement according to claim 1, wherein the layers are arranged to reflect different wavelengths.

* * * * *